(12) United States Patent
Watanabe et al.

(10) Patent No.: US 7,465,297 B2
(45) Date of Patent: Dec. 16, 2008

(54) SANITARY NAPKIN

(75) Inventors: Hitoshi Watanabe, Mitoyo-gun (JP);
Wataru Yoshimasa, Mitoyo-gun (JP);
Toshiyuki Tanio, Mitoyo-gun (JP);
Kenichiro Kuroda, Mitoyo-gun (JP);
Shinobu Fujikawa, Mitoyo-gun (JP)

(73) Assignee: Uni-Charm Corporation,
Shikokuchuo-Shi, Ehime (JP)

( * ) Notice: Subject to any disclaimer, the term of this patent is extended or adjusted under 35 U.S.C. 154(b) by 0 days.

(21) Appl. No.: 11/291,536

(22) Filed: Nov. 30, 2005

(65) Prior Publication Data

US 2006/0142724 A1 Jun. 29, 2006

(30) Foreign Application Priority Data

Dec. 28, 2004 (JP) .............................. 2004-378904

(51) Int. Cl.
*A61F 13/15* (2006.01)
*A61F 13/20* (2006.01)

(52) U.S. Cl. .......................... 604/385.101; 604/385.01; 604/385.17

(58) Field of Classification Search ............ 604/385.01, 604/367, 385.101, 378, 385.17, 385.03, 385.12, 604/385.14, 385.28
See application file for complete search history.

(56) References Cited

U.S. PATENT DOCUMENTS 4,046,147 A * 9/1977 Berg .................... 604/385.201
5,197,959 A 3/1993 Buell
6,371,948 B1 * 4/2002 Mizutani ................ 604/385.01

FOREIGN PATENT DOCUMENTS

| JP | 02-011139 A | 1/1990 |
| JP | 09-313529 A | 12/1997 |
| JP | 11-042250 A | 2/1999 |
| JP | 11-513921 A | 11/1999 |
| JP | 2000-083994 A | 3/2000 |
| JP | 2001-504727 A | 4/2001 |
| JP | 2002-301097 A | 10/2002 |
| JP | 2002-320638 A | 11/2002 |
| JP | 2003-093442 A | 4/2003 |
| WO | WO-98/00085 A1 | 1/1998 |
| WO | WO-98/22060 A1 | 5/1998 |
| WO | WO-02/087483 A1 | 11/2002 |

OTHER PUBLICATIONS

Office Action, dated Sep. 28, 2007, issued in U.S. Appl. No. 11/123,608.

* cited by examiner

*Primary Examiner*—Michele Kidwell
(74) *Attorney, Agent, or Firm*—Darby & Darby P.C.

(57) ABSTRACT

A sanitary napkin includes: a napkin body having a liquid-absorbent layer for absorbing and retaining liquid; and a projection projecting from a body surface of the napkin body. The projection has an apex and a pair of side wall portions formed of a liquid-permeable material. The apex is spaced apart from the body surface of the napkin body and extends along a longitudinal centerline of the napkin body. The side wall portions connect at the apex and diverge toward the body surface of the napkin body. The apex and the side wall portions are different in stiffness. The side wall portions have a space therebetween and are permitted to deform and approach each other.

8 Claims, 8 Drawing Sheets

SANITARY NAPKIN

INCORPORATION BY REFERENCE

The present application claims priority under 35 U.S.C. §119 to Japanese Patent Application No. 2004-378904 filed on Dec. 28, 2004 in the Japanese language, which is hereby incorporated by reference in its entirety.

BACKGROUND OF THE INVENTION

1. Field of the Invention

The present invention relates to a sanitary napkin with a projection disposed on a body surface of a napkin body and more particularly to a sanitary napkin whose projection can easily conform to the vaginal opening, the anus, and the intergluteal cleft so as to be effective in preventing leakage of menstrual blood.

2. Description of the Related Art

There have been known sanitary napkins with a napkin body containing a liquid-absorbent layer and a projection projecting from a body surface of the napkin body.

Japanese Unexamined Patent Application Publication No. 2001-504727 discloses a sanitary napkin in which a topsheet is disposed on a body surface of a liquid-absorbent layer, and an absorbent body and a stiffening element are interposed between the liquid-absorbent layer and the topsheet. The topsheet, the absorbent body, and the stiffening element form a hump having a generally triangular cross section.

Japanese Unexamined Patent Application Publication No. 2002-301097 discloses an absorbent article in which an absorbent body is disposed between a surface material and a backsheet. At its rear part, the absorbent article has a fold which can easily be deformed to project and fit in the intergluteal cleft of the wearer's body. The fold may be formed by embossing the absorbent body or folding the surface material in two. Providing an elastic member at the fold facilitates projection of the absorbent core or the surface material.

Japanese Unexamined Patent Application Publication No. 2002-320638 discloses a sanitary napkin in which a T-section three-dimensional wall formed of a liquid-permeable sheet is disposed on the body surface of the napkin body. This three-dimensional wall has elastic members for exerting a longitudinal contractive force and is raised from the body surface of the napkin body when the napkin body is curved with front and rear edges of the napkin body being drawn closer to each other by the elastic members.

Since the hump of the sanitary napkin disclosed in the Patent Publication No. 2001-504727 is constructed by interposing the absorbent body and the stiffening element between the liquid-absorbent layer and the topsheet, it is difficult to deform the hump to decrease the distance between two side wall portions. Therefore, the hump cannot easily fit in a deep cleft having a small opening angle such as intergluteal cleft. This tends to result in a clearance between the cleft and the hump, allowing menstrual blood to flow down the intergluteal cleft and causing rearward leakage such as during sleep. Moreover, the absorbent body and the stiffening element within the hump resist concave deformation of the sanitary napkin. Therefore, when worn in the crotch, the sanitary napkin tends to feel uncomfortable and leave a space between the rear part of the sanitary napkin and the wearer's body.

In the absorbent article disclosed in Patent Publication No. 2002-301097, the fold is provided in the rear part of the absorbent article so that it can easily fit in the intergluteal cleft. However, if the fold is formed by processing the absorbent core, it is difficult to project the fold with an acute angle, and therefore, the fold cannot easily fit in a narrow cleft such as the intergluteal cleft. If the fold is formed by folding the surface material in two, on the other hand, the fold becomes less resistant to a lateral compressive force. Therefore, the fold cannot easily follow the movement of the wearer's body, which makes it difficult to keep the fold in contact with the intergluteal cleft.

Since the three-dimensional wall disclosed in the Patent Publication No. 2002-320638 has a T-shaped section, it has the advantage that the liquid-permeable sheet of the three-dimensional wall can easily be kept in contact with the vaginal opening, but it is difficult to fit the central portion of the three-dimensional wall into a deep cleft having a small opening angle such as the intergluteal cleft.

SUMMARY OF THE INVENTION

The present invention has been developed to solve the problems in the prior art set forth above and has an object to provide a sanitary napkin with a projection whose opposing inclined side wall portions are permitted to deform freely so that the projection can easily conform to a cleft of varying depth.

According to the present invention, there is provided a sanitary napkin comprising:

a napkin body having a liquid-absorbent layer for absorbing and retaining liquid; and a projection projecting from a body surface of the napkin body, the projection having an apex and a pair of side wall portions formed of a liquid-permeable material, the apex being spaced apart from the body surface of the napkin body and extending along a longitudinal centerline of the napkin body, the side wall portions connecting at the apex and diverging toward the body surface of the napkin body, wherein the apex and the side wall portions are different in stiffness, and the side wall portions have a space therebetween and are permitted to deform and approach each other.

For example, the side wall portions may first diverge and subsequently converge from the apex toward the body surface of the napkin body.

In the sanitary napkin of the present invention, the projection having different stiffnesses between the apex and the side wall portions is superior in recovery from deformation and can easily conform to the contours of the wearer's body. In addition, since the side wall portions have a space therebetween and are permitted to deform and approach each other, the projection can easily fit in a deep cleft such as the intergluteal cleft.

In order that the side wall portions will fit against the wearer's skin within the intergluteal cleft, the side wall portions are preferably adapted to return to an opening angle of 20 degrees or more after removal of a compressive force of 2 kg per 10 cm×10 cm, which is laterally applied to the projection for 30 seconds to bring the side wall portions into contact with each other.

Also preferably, the projection is adapted to deform in accordance with deformation of the napkin body when front and rear ends of the napkin body approach each other to concavely curve the body surface of the napkin body.

The apex of the projection may include a longitudinally-extending central elastic member whose both ends are secured on the napkin body to exert a tension for causing deformation of the napkin body. With the central elastic member, stiffness may be increased at the apex of the projection so that the apex can easily find its way into a deep cleft such as the intergluteal cleft.

The projection may further include longitudinally-extending side elastic members on both sides of the central elastic member, the central elastic member may be spaced farther from the napkin body than the side elastic members, and the side wall portions may extend between the central elastic member and the respective side elastic members. With this arrangement of the central and side elastic members, the position of the side wall portions can be stabilized. This arrangement can also improve conformity of the project to the vaginal opening, the anus, and the intergluteal cleft.

In order to arrange the central and side elastic members as above, preferably, the individual central and side elastic members have front and rear connection points between which the elastic member remains unsecured on the napkin body, the front connection point of the individual side elastic members is located behind the front connection point of the central elastic member, and the rear connection point of the individual side elastic members is located forward of the rear connection point of the central elastic member.

Here, the central elastic member may exert a greater elastic tension than the individual side elastic members.

In the present invention, the projection may be fusion-bonded, compressed, or cut along the apex to make a difference in stiffness between the apex and the side wall portions. Alternatively, the side wall portions may have reinforcing members to make a difference in stiffness between the apex and the side wall portions.

In a natural state where no external force is exerted on the napkin body, preferably, a height of the projection from the body surface of the napkin body is maximized at a location behind a vagina-facing part of the sanitary napkin.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
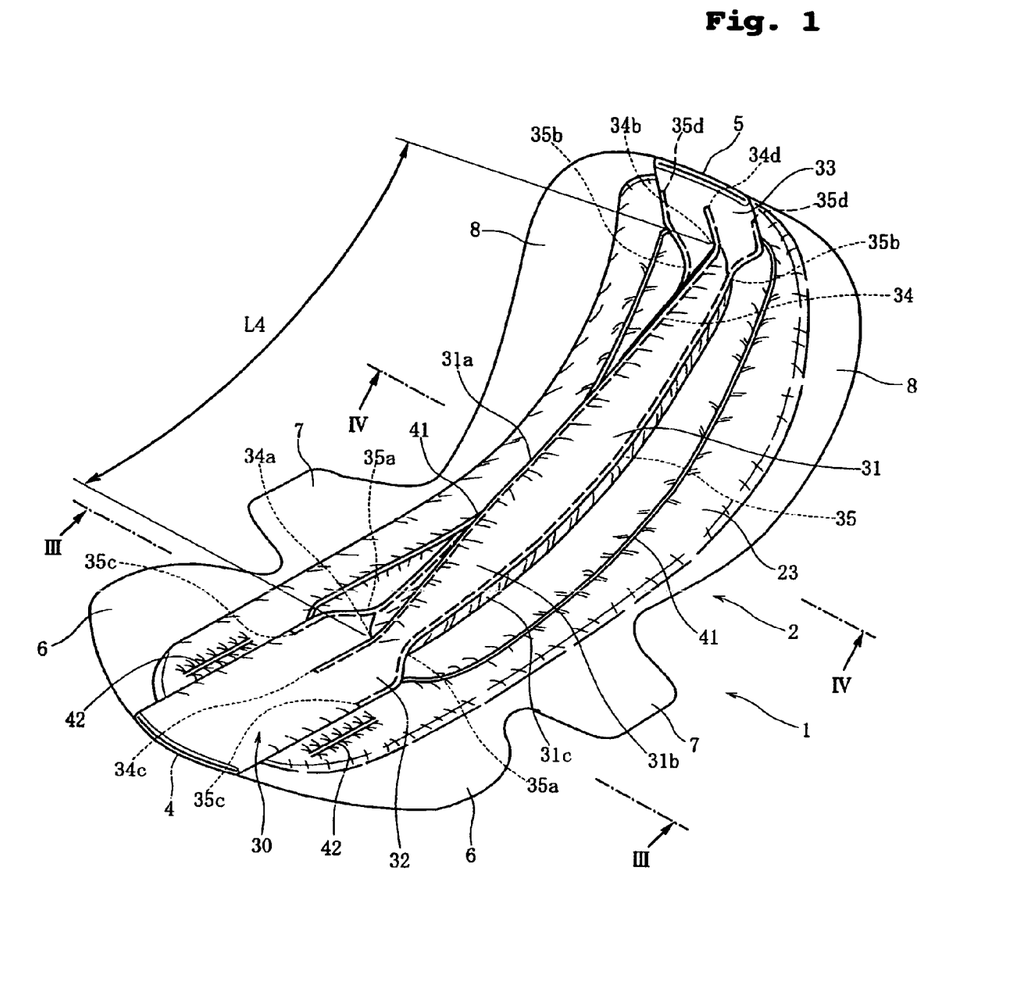
FIG. 1 is a perspective view of a sanitary napkin according to a first embodiment of the present invention in a natural state where no external force is exerted thereon.
Figure 2:
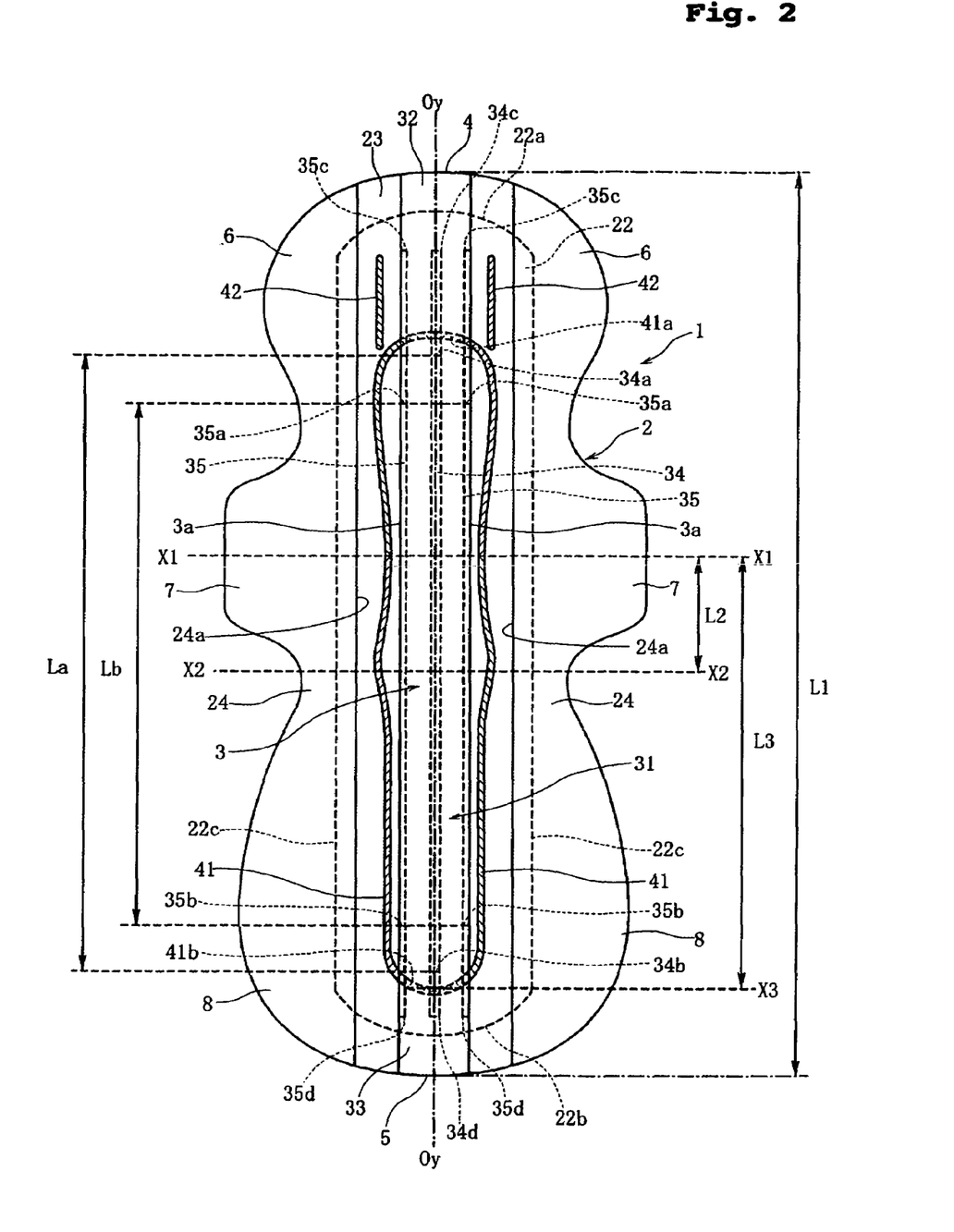
FIG. 2 is a plan view showing a body surface of a flattened sanitary napkin according to the first embodiment.
Figure 3:
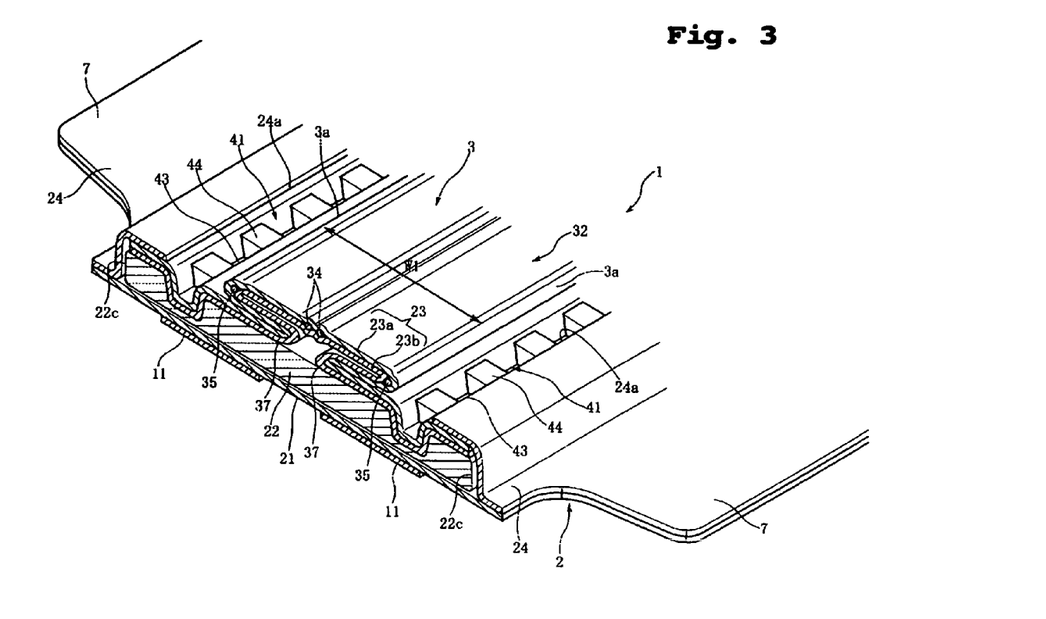
FIG. 3 is a sectional view taken along line III-III of FIG. 1.
Figure 4:
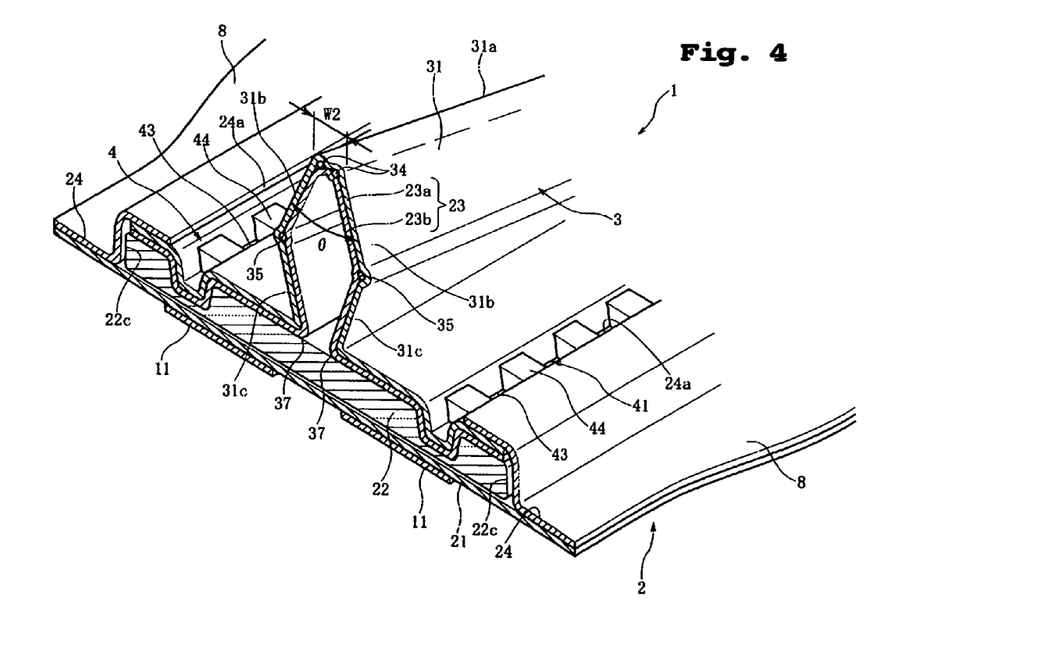
FIG. 4 is a sectional view taken along line IV-IV of FIG. 1.
Figure 5:
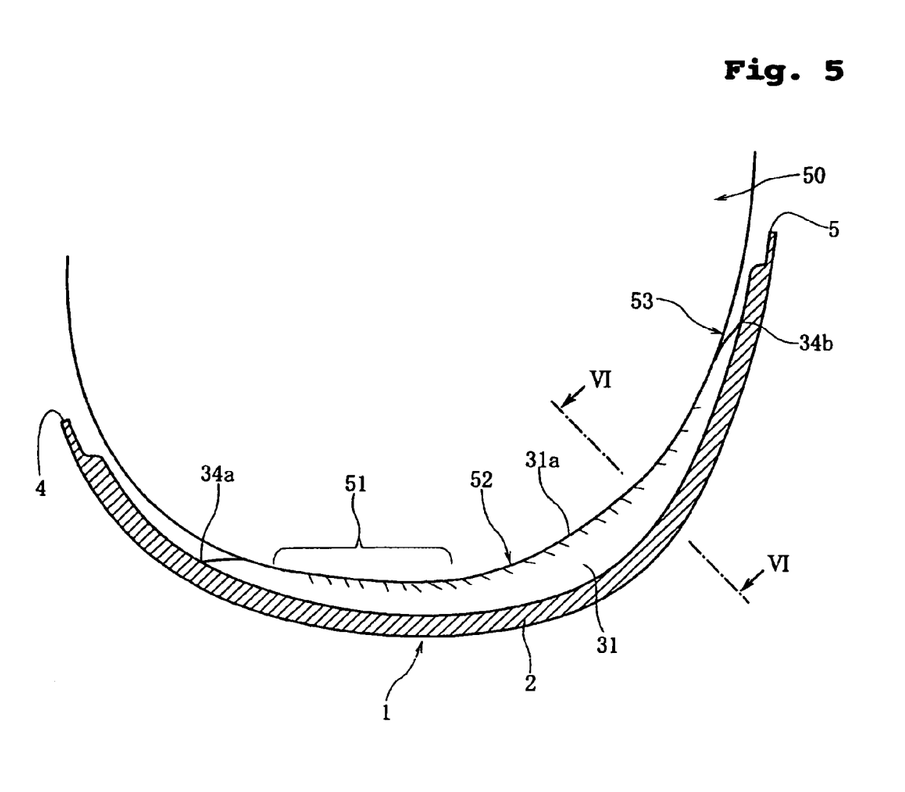
FIG. 5 is a longitudinal sectional view schematically showing a state where a sanitary napkin is applied to the woman's body.
Figure 6:
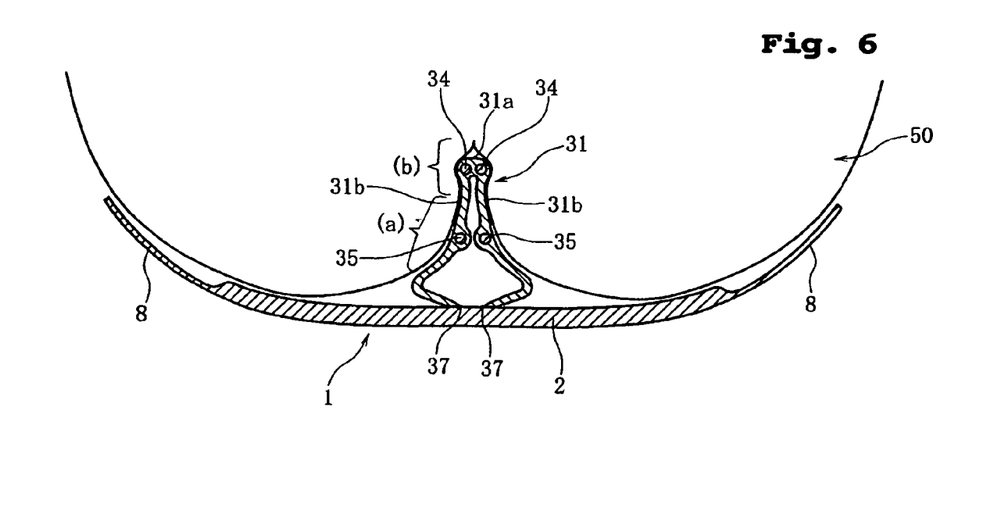
FIG. 6 is a sectional view taken along line VI-VI of FIG. 5.

FIG. 1 is a perspective view of a sanitary napkin 1 according to a first embodiment of the present invention in a natural state where no external force is exerted thereon. FIG. 2 is a plan view in which the sanitary napkin 1 is flattened. FIG. 3 is a sectional view taken along line III-III of FIG. 1, and FIG. 4 is a sectional view taken along line IV-IV of FIG. 1. FIG. 5 is a longitudinal sectional view schematically showing a state where the sanitary napkin 1 is applied to the woman's body from the crotch to the buttocks, and FIG. 6 is a sectional view taken along line VI-VI of FIG. 5.

It should be noted that the sanitary napkin, as well as its individual components, has two major surfaces: of which one surface intended to be worn toward the wearer's crotch is referred to as "body surface", while the other surface is referred to as "garment surface". In addition, the lengthwise direction of the sanitary napkin is referred to as "longitudinal direction", while the direction perpendicular to the longitudinal direction is referred to as "lateral direction". With respect to dimensions of the individual components, unless otherwise stated, a dimension measured in the longitudinal direction is referred to as "length", while a dimension measured in the lateral direction is referred to as "width".

The sanitary napkin 1 comprises a napkin body 2 and a surface element 3 disposed on the body surface of the napkin body 2 to form a projection.

As shown in FIGS. 3 and 4, the napkin body 2 includes a liquid-blocking backsheet 21 on the garment surface side of the napkin body 2, a liquid-absorbent layer 22 dispose on the backsheet 21, and a liquid-permeable topsheet 23 covering the liquid-absorbent layer 22. The surface element 3 is formed of a part of the topsheet 23.

As shown in FIG. 2, the napkin body 2 has arcuate front and rear edges 4, 5. The napkin body 2 is elongated to have a length L1 in the range of 280 to 450 mm. The liquid-absorbent layer 22 is also elongated to have arcuate front and rear edges 22a, 22b, which are spaced slightly inward from the front and rear edges 4, 5, respectively. Furthermore, the liquid-absorbent layer 22 has right and left side edges 22c, 22c, which extend linearly in parallel to a longitudinal centerline Oy. However, the shape of the right and left side edges 22c, 22c should not be understood as limited to this embodiment.

On laterally opposite sides of the liquid-absorbent layer 22, the napkin body 2 has laterally projecting front flaps 6, 6, laterally projecting fold-back flaps 7, 7, and laterally projecting rear flaps 8, 8 in order from front to rear. In the front flaps 6, 6, the fold-back flaps 7, 7, and the rear flaps 8, 8, the body surface of the backsheet 21 is covered with a liquid-blocking side sheet 24. The liquid-blocking side sheet 24 is bonded to the backsheet 21 through a hot-melt type adhesive.

As shown in FIGS. 3 and 4, the side sheets 24, 24 lie opposite one another with their opposing edges 24a, 24a located inside the side edges 22c, 22c of the liquid-absorbent layer 22 (i.e., located closer to the longitudinal centerline Oy than the side edges 22c, 22c). At the laterally opposite side portions of the liquid-absorbent layer 22, therefore, the body surface of the liquid-absorbent layer 22 is covered with the topsheet 23, and the body surface of the topsheet 23 is further covered with the side sheets 24, 24. In the area defined between the opposing edges 24a, 24a of the side sheets 24, 24, the liquid-permeable topsheet 23 is exposed externally. The overlap between this area and the liquid-absorbent layer 22 is called "main liquid-absorbent region."

X1 shown in FIG. 2 represents a vagina-facing reference line, and this vagina-facing reference line X1 is spaced 100 to 200 mm, preferably 100 to 140 mm, for example, about 120 mm, rearward from the front edge 4 of the napkin body 2.

The vagina-facing reference line X1 as used herein is a target position with which the center of the vaginal opening is to almost coincide when wearing the sanitary napkin 1 along with an undergarment. Leading to this target is through the contour of the sanitary napkin as viewed from the body surface side or the whole design including the arrangement of compression lines on the body surface. Particularly when the fold-back flaps 7, 7 are provided as in the present embodiment, the target usually coincides with the longitudinal centers of the fold-back flaps 7, 7. In the present embodiment, the line passing through the longitudinal centers of the fold-back flaps 7, 7 is taken as the vagina-facing reference line X1.

X2 shown in FIG. 2 represents an anus-facing reference line, and this anus-facing reference line X2 is intended to face the anus when the vagina-facing reference line X1 coincides with the center of the vaginal opening. The anus-facing reference line X2 is usually spaced a distance L2 of 30 to 70 mm, which varies depending on the wearer's body, rearward from the vagina-facing reference line X1.

X3 shown in FIG. 2 represents a coccyx-facing reference line. This coccyx-facing reference line X3 is intended to face the coccyx when the vagina-facing reference line X1 coincides with the center of the vaginal opening. The coccyx-facing reference line X3 is usually spaced a distance L3 of 120 to 180 mm, which varies depending on the wearer's body, rearward from the vagina-facing reference line X1. For example, the coccyx-facing reference line X3 may be spaced 330 mm rearward from the front edge 4 and 175 mm rearward from the vagina-facing reference line X1. The rear edge 5 of the napkin body 2 and the rear edge 22b of the liquid-absorbent layer 22 are located behind the coccyx-facing reference line X3.

Between the vagina-facing reference line X1 and the coccyx-facing reference line X3, the napkin body 2 is intended to face the vaginal opening, the anus, and the intergluteal cleft. Throughout the disclosure, the cleft extending from forward of the vaginal opening to adjacent the coccyx in the woman's body is merely called "cleft", while the cleft extending from the anus to the coccyx is called "intergluteal cleft". The napkin body 2 is intended to face the intergluteal cleft over a length of 50 to 150 mm.

The backsheet 21 may be a film, for example, a polyethylene resin film having a basis weight of about 23 g/m$^2$, and is preferably permeable to moisture. The liquid-absorbent layer 22 may be a mixture of fluff pulp and superabsorbent polymer (SAP) wrapped in a hydrophilic tissue having a basis weight of 18 g/m$^2$. The fluff pulp may have a weight of about 400 g/m$^2$; the SAP may have a weight of about 12 g/m$^2$. The side sheet 24 may be a spunbonded nonwoven fabric made of polyethylene/polypropylene sheath/core bicomponent fibers.

The topsheet 23 may be a laminate of first and second liquid-permeable sheets 23a, 23b. The first and second liquid-permeable sheets 23a, 23b may each be a through-air bonded nonwoven fabric having a basis weight of about 25 g/m$^2$. The through-air bonded nonwoven fabric may be made of polyethylene/polyethylene terephthalate sheath/core bicomponent fibers with an inorganic filler such as titanium oxide mixed into the core of polyethylene terephthalate. Preferably, 80% of the sheath/core bicomponent fibers are made hydrophilic by coating of a hydrophilic lubricant; 20% of the sheath/core bicomponent fibers are made water-repellent by coating of a water-repellent lubricant.

In order to prevent separation, the first and second liquid-permeable sheets 23a, 23b may be bonded to each other through a hot-melt type adhesive which is applied to such an extent as not to interfere with liquid passage (e.g., in an amount of 2 g/m$^2$).

The liquid-permeable sheet for the topsheet 23 is not limited to the above-mentioned through-air bonded nonwoven fabric. For example, there may be used a point-bonded, spunlaced, or spunbonded nonwoven fabric. Here, the fiber density is preferably 0.12 g/cm$^3$ or less and the basis weight preferably falls within the range of 15 to 60 g/m$^2$ so as to improve liquid-permeability. Alternatively, there may be used a resin film formed with a large number of apertures for liquid passage. If desired, the apertured resin film may be used as the first liquid-permeable sheet 23a, while the nonwoven fabric such as through-air bonded may be used as the second liquid-permeable sheet 23b. The topsheet 23 may be embossed in a dot pattern or corrugated.

As shown in FIGS. 3 and 4, boundaries 37, 37 extend in parallel to the longitudinal direction at locations spaced an equal distance laterally from the longitudinal centerline Oy. Outside the boundaries 37, 37, the topsheet 23 is bonded to the body surface of the liquid-absorbent layer 22. Between the boundaries 37, 37, on the other hand, the topsheet 23 remains unbonded to the body surface of the liquid-absorbent layer 22, providing the surface element 3.

FIG. 2 shows a state where the sanitary napkin 1 is flattened to stretch the backsheet 21 on a plane. Here, the surface element 3 is folded flat on the body surface of the napkin body 2 so as to extend longitudinally in the form of a strip, as shown in FIG. 3.

In the surface element 3, two central elastic members 34 are disposed between the first and second liquid-permeable sheets 23a, 23b. The central elastic members 34 are laterally slightly spaced apart and extend along the longitudinal centerline Oy. The central elastic members 34 may be bonded to the first and second liquid-permeable sheets 23a, 23b through a hot-melt type adhesive. In FIG. 2, the two central elastic members 34 are shown as if a single component for the sake of convenience of drawing. Between a front end 34c and a front connection point (or front footpoint) 34a behind the front end 34c, the central elastic members 34, as well as the topsheet 23, are secured on the body surface of the napkin body 2 through a hot-melt type adhesive. Between a rear end 34d and a rear connection point (or rear footpoint) 34b forward of the rear end 34d, the central elastic members 34, as well as the topsheet 23, are also secured on the body surface of the napkin body 2 through a hot-melt type adhesive.

At fold lines 3a, 3a which are created by folding flat the surface element 3 on the body surface of the napkin body 2, as shown in FIGS. 3 and 4, side elastic members 35 are disposed between and bonded to the first and second liquid-permeable sheets 23a, 23b through a hot-melt type adhesive. When the surface element 3 is folded flat, the side elastic members 35 are spaced an equal distance laterally from the central elastic members 34 in parallel relation to one another.

Between a front end 35c and a front connection point (or front footpoint) 35a behind the front end 35c, the side elastic members 35, as well as the topsheet 23, are secured on the body surface of the napkin body 2 through a hot-melt type adhesive. Between a rear end 35d and a rear connection point (or rear footpoint) 35b forward of the rear end 35d, the side elastic members 35, as well as the topsheet 23, are also secured on the body surface of the napkin body 2 through a hot-melt type adhesive.

The front connection points 35a of the side elastic members 35 are located behind the front connection points 34a of the central elastic members 34. The rear connection points 35b of the side elastic members 35 are located forward of the rear connection points 34b of the central elastic members 34.

When no external force is exerted on the sanitary napkin 1, the central elastic members 34 exert an elastic tension between the front and rear connection points 34a, 34b to draw the front and rear connection points 34a, 34b closer to each other. Likewise, the side elastic members 35 exert an elastic tension between the front and rear connection points 35a, 35b to draw the front and rear connection points 35a, 35b closer to each other.

As a result, as shown in FIG. 1, the body surface of the napkin body 2 is concavely curved. Here, the central elastic members 34 move away from the body surface of the napkin body 2 over a length La between the front and rear connection points 34a, 34b, while the side elastic members 35 move away from the body surface of the napkin body 2 over a length Lb between the front and rear connection points 35a, 35b. Therefore, the topsheet 23 of the surface element 3 is raised from the body surface of the napkin body 2 by the raised portions of the elastic members 34, 35, forming a hollow projection 31.

Forward of the front connection points 34a of the central elastic members 34, as shown in FIG. 3, the topsheet 23 of the surface element 3 is secured on the body surface of the napkin body 2 in the folded state, forming a front flat portion 32. Behind the rear connection points 34b of the central elastic members 34, the topsheet 23 of the surface element 3 is also secured on the body surface of the napkin body 2 in the same folded state as shown in FIG. 3, forming a rear flat portion 33. In FIG. 3, the width of the front flat portion 32 between the fold lines 3a, 3a is indicated by W1.

As shown in the cross section of FIG. 4, the projection 31 has an apex 31a which is provided with the central elastic members 34, 34 and spaced farthest from the body surface of the napkin body 2. The apex 31a extends along the longitudinal centerline Oy.

In the projection 31, the side elastic members 35, 35 are located at a level closer to the body surface of the napkin body 2 than the central elastic members 34, 34. Between the central elastic members 34, 34 and the side elastic members 35, 35, the projection 31 has upper side wall portions 31b, 31b formed of the topsheet 23. As the upper side wall portions 31b, 31b extend from the apex 31a toward the body surface of the napkin body 2, the lateral distance between the upper side wall portions 31b, 31b gradually increases. In other words, the upper side wall portions 31b, 31b diverge toward the body surface of the napkin body 2. The upper side wall portions 31b, 31b provide inclined wall surfaces at an opening angle θ. Thus, the projection 31 has a wedge formed of the apex 31a and the upper side wall portions 31b, 31b. Here, the opening angle θ refers to an angle formed between the outer surfaces of the upper side wall portions 31b, 31b.

Between the side elastic members 35, 35 and the boundaries 37, 37, the projection 31 has lower side wall portions 31c, 31c formed of the topsheet 23. As shown in FIG. 4, the lower side wall portions 31c, 31c are inclined to gradually decrease the distance toward the body surface of the napkin body 2. In other words, the lower side wall portions 31c, 31c converge toward the body surface of the napkin body 2.

As shown in FIGS. 1 and 2, the front connection point 34a of the central elastic member 34 becomes a front rising point of the projection 31; the rear connection point 34b of the central elastic member 34 becomes a rear rising point of the projection 31. The front connection point 34a is located forward of the vagina-facing reference line X1 of the napkin body 2; the rear connection point 34b is located on or slightly forward of the coccyx-facing reference line X3. Thus, the projection 31 extends the length La between the front and rear connection points 34a, 34b.

The projection 31 is intended to face the wearer's body from the vaginal opening or from forward of the vaginal opening to the intergluteal cleft, past the anus. The rising height of the projection 31 from the body surface of the napkin body 2 to the apex 31a is maximized near the midpoint between the front and rear connection points 34a, 34b, i.e., behind the vagina-facing reference line X1. Preferably, the location where the rising height of the projection 31 is maximized is not spaced more than 10 mm from the anus-facing reference line X2.

The front connection point 34a is preferably spaced 35 to 150 mm forward from the anus-facing reference line X2; the rear connection point 34b is preferably spaced 35 to 150 mm rearward from the anus-facing reference line X2. Thus, the length La of the projection 31 preferably falls within the range of 70 to 300 mm. If the length La is smaller than 70 mm, it will be difficult to raise the projection 31 from the body surface of the napkin body 2 to a sufficient height. If the length La is greater than 300 mm, the projection 31 will be raised too high and tend to feel uncomfortable against the wearer's body.

The central and side elastic members 34, 35 may be thread-like materials, for example, polyurethane elastic filaments having a fineness in the range of 420 to 10000 dtex, preferably in the range of 1800 to 8000 dtex. Alternatively, they may be rubber threads, such as of natural rubber or synthetic rubber. If desired, the central and side elastic members 34, 35 may be made by bundling or twisting a plurality of thin elastic filaments. In this case, the respective elastic members may be prepared such that the total fineness of the thin elastic filaments falls within the above range. Between the front and rear connection points 34a, 34b, the central elastic members 34, 34 are bonded to the first and second liquid-permeable sheets 23a, 23b while being stretched at least 1.2 times, preferably at least 1.5 times the original length. Between the front and rear connection points 35a, 35b, likewise, the side elastic members 35, 35 are bonded to the first and second liquid-permeable sheets 23a, 23b while being stretched at least 1.2 times, preferably at least 1.5 times the original length.

Figure 7:
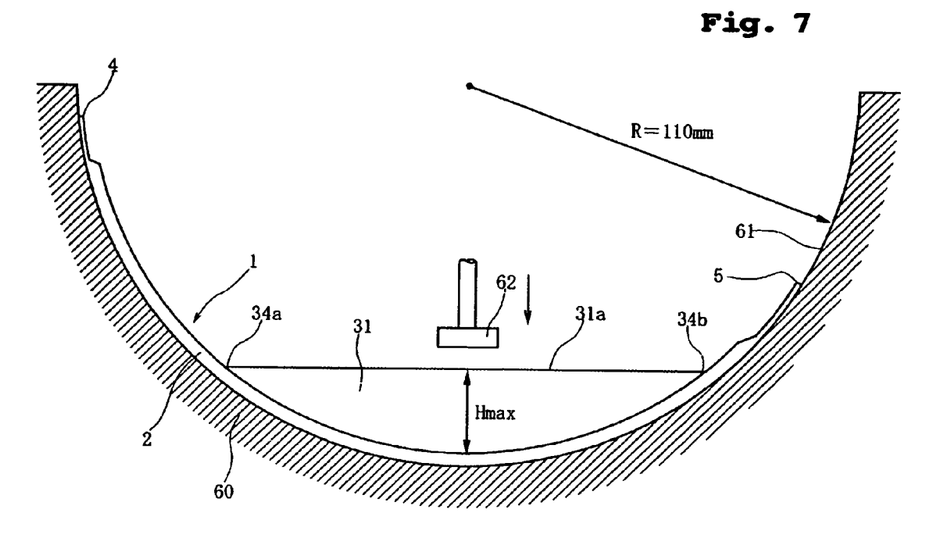
FIG. 7 is a view schematically showing a method for measuring an elastic contractive force exerted by an elastic member provided in a projection of a sanitary napkin.

The tension exerted by each central elastic member 34 between the front and rear connection points 34a, 34b may be equal to the tension exerted by each side elastic member 35 between the front and rear connection points 35a, 35b, and the elastic tension exerted by each elastic member is preferably about 0.1 to 5.0 N when the sanitary napkin 1 is flattened, as shown in FIG. 2. If the tension is below the above range, it will be difficult for the sanitary napkin 1 in a natural state to curve into such a shape as shown in FIG. 1. If the tension is above the above range, there is a possibility of giving an uncomfortable feeling to the wearer's body. For example, when the sanitary napkin 1 is flattened, the central and side elastic members 34, 35 may each exert a tension of about 0.8 N. When the backsheet 21 of the napkin body 2 is adhered to a cylindrical surface having a radius R of 110 mm, as shown in FIG. 7, the central and side elastic members 34, 35 may each exert a tension of about 0.6 N.

Alternatively, the central elastic member 34 may be adapted to exert a larger elastic tension than the individual side elastic members 35 so that the upper side wall portions 31b, 31b can easily be inclined to form a wedge, as shown in FIG. 4.

The width W1 of the front flat portion 32 may be in the range of 10 to 60 mm. The rear flat portion 33 may have the same width W1 as the front flat portion 32.

On the body surface of the napkin body 2, as shown in FIGS. 1 and 2, there are provided main and front compression lines 41, 42. These compressed lines 41, 42 are formed by pressing and heating the topsheet 23 and the liquid-absorbent layer 22 at the same time. The main compression lines 41 may extend continuously with their front ends on or slightly forward of the front connection point 34a of the central elastic member 34 and with their rear ends on or slightly behind the rear connection point 34b of the central elastic member 34. The front compression lines 42 are located forward of the main compression lines 41.

As shown in FIG. 2, the main compression lines 41 are connected together through front and rear connections 41a, 41b to enclose an elongated area overlapping the liquid-absorbent layer 22. The main compression lines 41 function as a stiffening element. With the main compression lines 41, the napkin body 2 can be stiffened to resist the elastic contractive force exerted by the central and side elastic members 34, 35. Thus, the napkin body 2 can be prevented from folding between the front and rear connection points 34a, 34b.

As shown in FIGS. 3 and 4, the main compression line 41 alternates longitudinally between highly compressed portions 43 and less highly compressed portions 44, wherein the body surface of the napkin body 2 is recessed more deeply in the highly compressed portions 43 than in the less highly compressed portions 44. In the highly compressed portions 43, the liquid-absorbent layer 22 is compressed to have a density at least 2 times, preferably at least 5 times the original density. In the less highly compressed portions 44, which has a lower density than the highly compressed portions 43, the liquid-absorbent layer 22 is compressed to have a density at least 1.5 times, preferably at least 2 times the original density.

As shown in FIGS. 3 and 4, the napkin body 2 has pressure-sensitive adhesive layers 11 on the garment surface of the backsheet 21 for adhesion to an undergarment. The pressure-sensitive adhesive layers 11 extend parallel to and on both sides of the longitudinal centerline Oy. The pressure-sensitive adhesive layers 11 are in the shape of strips and extend the entire length of the napkin body 2.

Although omitted in the drawings, it should be noted that the fold-back flaps 7, 7 and the rear flaps 8, 8 also have pressure-sensitive adhesive layers on the garment surface of the backsheet 21.

FIG. 7 shows a measurement device 60 whose concave cylindrical surface 61 has a radius R of 110 mm. The radius R of 110 mm almost corresponds to the average radius of longitudinal curvature of the cleft of an adult woman who is 27 years old, stands 168 cm tall, weights 56 kg, and has a BMI (body mass index) of 19.8. Here, the BMI is a value obtained by weight(kg)/height(m)$^2$.

The garment surface of the napkin body 2 is fixed on the cylindrical surface 61 through the pressure-sensitive adhesive layers 11 with the longitudinal direction of the sanitary napkin 1 being oriented along a direction of curvature of the cylindrical surface 61. At this time, the height of the projection 31 measured radially of the cylindrical surface 61 from the body surface of the napkin body 2 to the apex 31a may be a maximum $H_{max}$ of 10 to 60 mm, preferably 15 to 40 mm.

Figure 8:
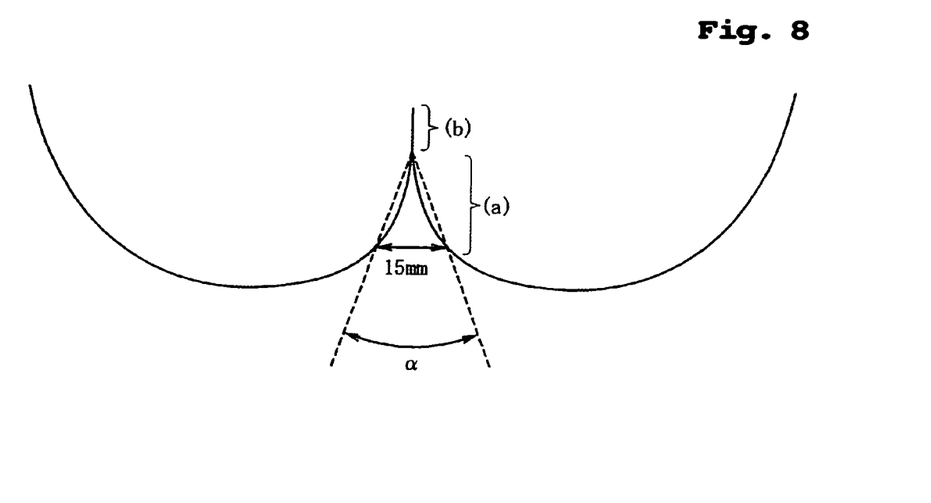
FIG. 8 is a view schematically showing a state where a projection is fitted into a cleft of the woman's body.

FIG. 8 is a schematic diagram showing the crotch of the above adult woman. In both a standing position and a supine position, the cleft of the crotch has a contact portion (b) where the opposing surfaces of the skin are kept in contact with each other and a noncontact portion (a) where the opposing surfaces of the skin diverge outwardly. In the crotch of the adult woman, between a location forward of the vaginal opening and a location spaced 80 mm rearward from the anus, the noncontact portion (a) has a depth of about 10 to 25 mm in the standing position and about 5 to 20 mm in the supine position. The total depth of the noncontact portion (a) and the contact portion (b) becomes a maximum of about 35 to 45 mm between a location adjacent the anus and a location spaced 25 mm rearward from the anus.

Therefore, if the maximum $H_{max}$ of the height of the projection 31 falls within the range of 10 to 60 mm (preferably within the range of 15 to 40 mm), the projection 31 in both the standing position and the supine position can easily fit to the noncontact portion (a) at the vaginal opening, the anus, and the intergluteal cleft. If the maximum $H_{max}$ is more than 10 mm, the apex 31a of the projection 31 can make its way into the contact portion (b).

For measurement, there may be used a pusher 62 that moves straight radially of the cylindrical surface 61. The pusher 62 has a 30 mm diameter circular plane, which is intended to face an object to be pushed. At the location where the rising height from the body surface of the napkin body 2 becomes the maximum $H_{max}$, the projection 31 is pushed straight by the pusher 62 at a rate of 20 mm/min radially of the cylindrical surface 61.

The force required to depress the projection 31 until the height from the body surface of the napkin body 2 becomes 10 mm is preferably in the range of 0.1 to 5 N, more preferably in the range of 0.3 to 2.0 N. Since the depth of the noncontact portion (a) is at least about 10 mm, as set forth above, when the sanitary napkin 1 is worn, the projection 31 may be depressed until the height from the body surface of the napkin body 2 becomes 10 mm. If the force required at this time falls within the above range, the projection 31 hardly gives an unpleasant feeling to the crotch.

In addition, if the force required to depress the apex 31a of the projection 31 15 mm from the natural state radially of the cylindrical surface 61 is 0.3 N or more, the apex 31a of the projection 31 can easily make its way into the contact portion (b).

The apex 31a of the projection 31 preferably has a width W2 in the range of 1 to 3 mm. As shown in FIG. 4, the width W2 is measured at a location where the central elastic members 34 are arranged side-by-side. If the width W2 falls within the above range, the apex 31a of the projection 31 can easily make its way into the noncontact portion (a) and the contact portion (b).

As shown in FIG. 8, the noncontact portion (a) has an opening angle α. This angle is determined such that two imaginary lines meeting at the boundary between the noncontact portion (a) and the contact portion (b) are set to cross the skin where the opposing surfaces are spaced 15 mm apart from each other. These imaginary lines are shown by dashed lines in FIG. 8.

The opening angle α is about 100 degrees at the center of the vaginal opening, about 25 to 35 degrees near the anus, and about 40 to 60 degrees at the intergluteal cleft. Accordingly, if the opening angle θ between the upper side wall portions 31b, 31b (see FIG. 4) is 20 degrees or more (preferably 30 degrees or more) at the location of the maximum $H_{max}$, the upper side wall portions 31b, 31b of the projection 31 can easily fit against the opposing surfaces of the skin at the noncontact portion (a). Moreover, when fitted into the noncontact portion (a), the projection 31 may be further pressed toward the body surface of the napkin body 2 to keep the upper side wall portions 31b, 31b in contact with the opposing surfaces of the skin at the noncontact portion (a).

The upper limit of the opening angle θ at the location of the maximum $H_{max}$ may be about 120 degrees. Within this range, the projection 31 can easily fit on the vaginal opening. Moreover, when the apex 31a comes into the noncontact portion (a), the upper side wall portions 31b, 31b can easily be deformed to approach each other by the opposing surfaces of the skin. Thus, the projection 31 can easily be kept within the noncontact portion (a).

Here, the opening angle θ preferably returns to 20 degrees or more, more preferably 30 degrees or more, after removal of a load of 2 kg per 10 cm×10 cm, which is laterally applied to the projection 31 for 30 seconds with center at the location of the maximum $H_{max}$ to bring the upper side wall portions 31b, 31b, as well as the side elastic members 35, 35, into contact with each other. With such resilience, even if the projection 31 is laterally compressed within the noncontact portion (a) and then the opposing surfaces of the skin are opened again, the upper side wall portions 31b, 31b can easily be kept in contact with the skin within the noncontact portion (a).

When using the sanitary napkin 1, the pressure-sensitive adhesive layers 11 on the garment surface of the napkin body 2 are adhered to the inner side of the undergarment. Then, the fold-back flaps 7, 7 are folded back upon the outer side of the undergarment along two side edges of a crotch part of the undergarment and then the pressure-sensitive adhesive layers on the garment surfaces of the fold-back flaps 7, 7 are adhered to the outer side of the crotch part. In addition, the pressure-sensitive adhesive layers on the garment surfaces of the rear flaps 8, 8 are adhered to the inner side of the undergarment at a lower part of a back body.

When the sanitary napkin 1 is adhered to the undergarment by a user, the vagina-facing reference line X1 serves as a target for positioning so that it can be worn with the vagina-facing reference line X1 almost coinciding with the longitudinal center of the vaginal opening.

FIG. 5 shows a state where the sanitary napkin 1 is applied to a woman's body 50 along the cleft extending from the crotch to the buttocks. In FIG. 5, the vaginal opening is indicated by 51, the anus is indicated by 52, and the coccyx is indicated by 53. The intergluteal cleft extends from adjacent the anus 52 to the coccyx 53 in the woman's body 50.

In the sanitary napkin 1, the central elastic members 34 exert an elastic contractive force between the front and rear connection points 34a, 34b, so that the body surface of the napkin body 2 is concavely curved with the front and rear connection points 34a, 34b being drawn closer to each other.

As set forth above, since the hollow projection 31 is constructed of the central elastic members 34, the side elastic members 35, and the flexible first and second liquid-permeable sheets 23a, 23b, the cross section of the projection 31 can easily be deformed in accordance with the shape of the cleft.

At the location of the maximum height $H_{max}$, the projection 31 faces the anus 52 or slightly behind the anus 52. At and forward of the vaginal opening 51, the height of the projection 31 is relatively small and the upper side wall portions 31b, 31b of the projection 31 are laterally spread prior to contact with the wearer's body. Therefore, the projection 31 can fit against the vaginal opening 51 and its surroundings while being slightly crushed toward the napkin body 2.

At and slightly behind the anus 52, as shown in FIG. 6, the apex 31a of the projection 31 easily comes into the intergluteal cleft to introduce the upper side wall portions 31b, 31b into the noncontact portion (a) and bring them into contact with the skin within the noncontact portion (a). Furthermore, the apex 31a can easily make its way into the contact portion (b) due to the tension exerted by the central elastic members 34.

Since the projection 31 has a hollow wedge which is formed of the apex 31a having the width W2 and the upper side wall portions 31b, 31b inclined to diverge toward the napkin body 2, the projection 31 can easily be deformed in accordance with deformation of the cleft and kept in contact with the cleft, as shown in FIG. 6.

Menstrual blood discharged from the vaginal opening passes through spaces between fibers of the liquid-permeable sheets 23a, 23b under force of gravity and is quickly absorbed and retained due to hydrophilicity of the underlying liquid-absorbent layer 22. Although the menstrual blood tends to flow rearward from the vaginal opening during sleep, it can be collected by the projection 31 near or behind the anus 52. The menstrual blood given to the projection 31 passes through or flows down the liquid-permeable sheets 23a, 23b to reach the body surface of the napkin body 2 and is then quickly absorbed and retained by the liquid-absorbent layer 22. Thus, the menstrual blood is effectively prevented from leaking rearward from the sanitary napkin 1.

Hereinbelow, other embodiments of the sanitary napkin according to the present invention will be described. In the following embodiments, the detailed description of the portions having the same construction as those of the first embodiment will be omitted.

Figure 9:
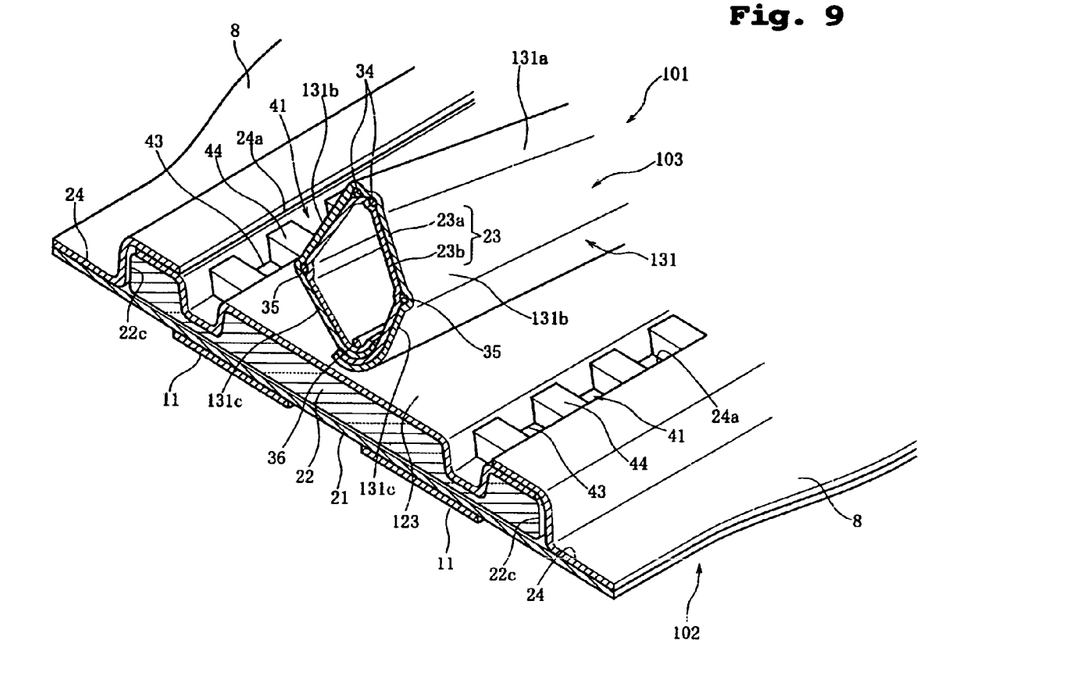
FIG. 9 is a sectional view showing a sanitary napkin according to a second embodiment of the present invention.

FIG. 9 is a sectional view corresponding to FIG. 4, showing a sanitary napkin 101 according to a second embodiment of the present invention.

The sanitary napkin 101 comprises a napkin body 102 and a projection 131 formed of a surface element 103. The surface element 103 is formed of the first and second liquid-permeable sheets 23a, 23b with the two central elastic members 34 and the two side elastic members 35 bonded therebetween. The front and rear connection points 34a, 34b of the central elastic members 34 and the front and rear connection points 35a, 35b of the side elastic members 35 are located as in the first embodiment shown in FIG. 2.

In the second embodiment, however, at least a part of the projection 131 is separated from the body surface of the napkin body 102 between the front and rear connection points 35a, 35b of the side elastic members 35 so as to be able to move laterally above the napkin body 102. In more detail, the body surface of the liquid-absorbent layer 22 is covered with a liquid-permeable topsheet 123 that is separate from the topsheet 23 of the surface element 103. Forward of the front connection points 35a and behind the rear connection points 35b, the surface element 103 is folded flat and secured on the body surface of the napkin body 102.

The projection 131 has an apex 131a, upper side wall portions 131b, 131b, and lower side wall portions 131c, 131c. The apex 131a includes the central elastic members 34, 34, and the upper side wall portions 131b, 131b extend between the central elastic members 34, 34 and the side elastic members 35, 35. The upper side wall portions 131b, 131b are inclined to gradually increase the lateral distance from the apex 131a toward the body surface of the napkin body 102. Below the upper side wall portions 131b, 131b, the lower side wall portions 131c, 131c are provided to gradually decrease the lateral distance toward the napkin body 102. At the bottom of the projection 131, the opposite edges of the topsheet 23 are bonded to each other, and a bottom elastic member 36 is provided on this bond. The bottom elastic member 36 extends longitudinally with both ends secured on the body surface of the napkin body 102. The bottom elastic member 36 is adapted to exert a smaller tension than the central and side elastic members 34, 35.

In the sanitary napkin 101 according to the second embodiment, even when the napkin body 102, which is adhered to the undergarment, is moved laterally by slippage of the undergarment, a fit of the projection 131 in the intergluteal cleft can easily be maintained. Therefore, even when the undergarment gets out of position by turning over in bed, the menstrual blood tending to migrate rearward along the intergluteal cleft can be effectively prevented from leaking.

Figure 10:
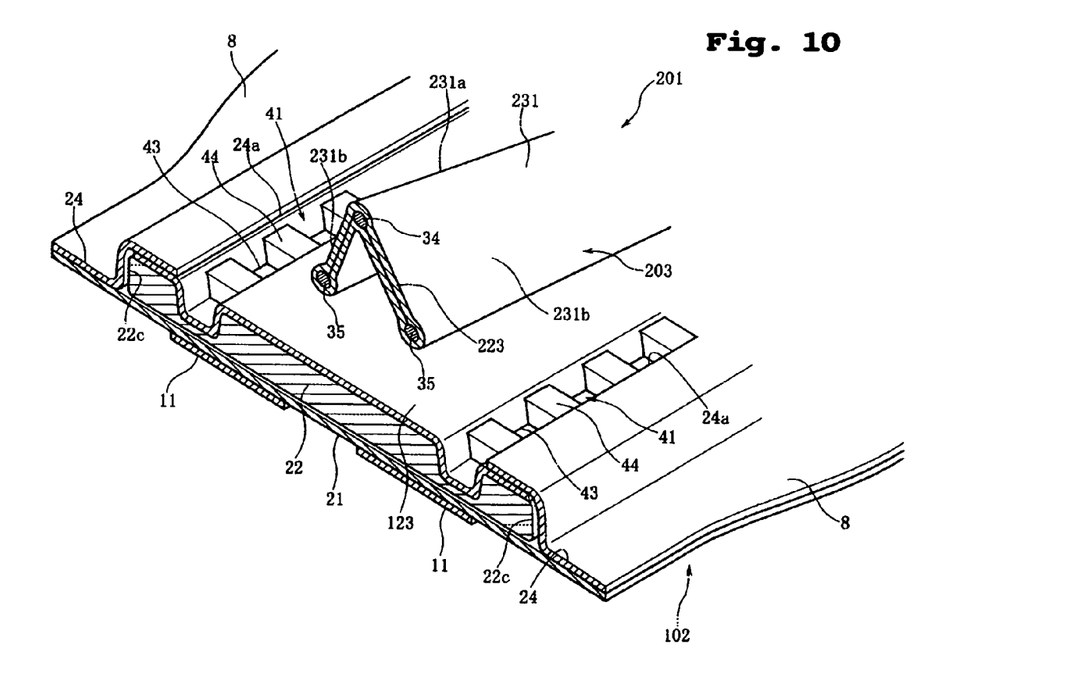
FIG. 10 is a sectional view showing a sanitary napkin according to a third embodiment of the present invention.

FIG. 10 shows a sanitary napkin 201 according to a third embodiment of the present invention.

The sanitary napkin 201 comprises the napkin body 102 and a projection 231 formed of a surface element 203. The napkin body 102 is identical to that of FIG. 9. The surface element 203 is formed by folding a topsheet 223 which is a single liquid-permeable sheet. The topsheet 223 is provided with the central and side elastic members 34, 35. Also in the third embodiment, at least a part of the projection 231 is separated from the body surface of the napkin body 102 between the front and rear connection points 35a, 35b of the side elastic members 35 so as to be able to move laterally above the napkin body 102.

The projection 231 has an inverted V-shaped cross section with one central elastic member 34 at an apex 231a so that side wall portions 231b, 231b are inclined to extend between the apex 231a and the respective side elastic members 35.

In order to snugly fit against the opposing surfaces of the skin at the noncontact portion (a) and easily make its way into the contact portion (b), the side wall portions 231b, 231b make the opening angle θ as in the first embodiment.

FIGS. 11(A) to 13(B) show other constructions of the projection. In portions not shown in the drawings, the projections may have the same construction as the first or second embodiment. If desired, the projections may have the same construction as the third embodiment.

Figure 11A:
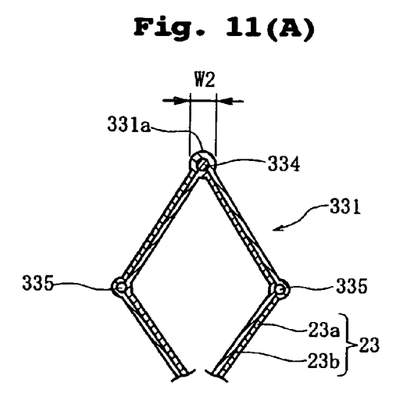
FIGS. 11(A) and 11(B) are partial sectional views showing other embodiments of a projection.

In the embodiment shown in FIG. 11(A), although both central and side elastic members 334, 335 are elastic filaments, the cross-sectional area of the central elastic member 334 is larger than that of the side elastic member 335. By using such a thick filament as the central elastic member 334, the width W2 of an apex 331a can be suitably set within the range of 1 to 3 mm, so that the projection 331 can easily make its way into the contact portion (b) without irritating the skin.

Figure 11B:
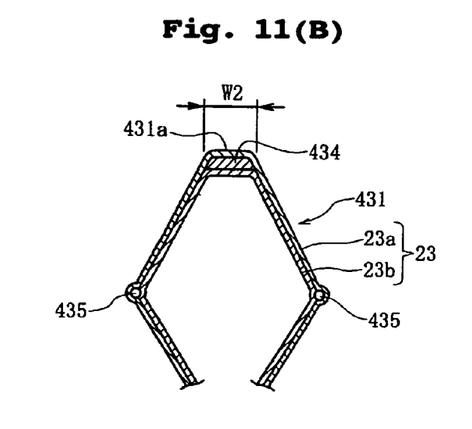

In the embodiment shown in FIG. 11(B), side elastic members 435 are similar to the side elastic members 335, but an elastic strip whose width is larger than thickness is used as a central elastic member 434. For the elastic strip, there may be used a film made of an elastic resin such as polyurethane, polyethylene, or synthetic rubber, or a composite material made by integrating the film to a nonwoven fabric such as of polyethylene fibers, polypropylene fibers, or polyester fibers such as by heat-embossing. Alternatively, there may be used a nonwoven fabric made of elastic fibers spun from the elastic resin and optionally other fibers. Since the central elastic member 434 is such an elastic strip, the width W2 of an apex 431a of a projection 431 can be suitably set as well.

In the embodiments shown in FIGS. 11(A) and 11(B), the tension exerted by the central elastic member 334/434 is preferably equal to the tension exerted by each side elastic member 335/435, but it is also possible that the tension exerted by the central elastic member 334/434 is greater than the tension exerted by each side elastic member 335/435.

Figure 12A:
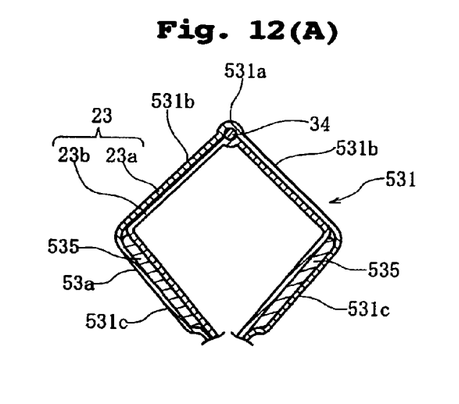
FIGS. 12(A) and 12(B) are partial sectional views showing other embodiments of a projection.

In the embodiment shown in FIG. 12(A), a projection 531 is formed of the topsheet 23 with the central elastic member 34 disposed between the first and second liquid-permeable sheets 23a, 23b to provide an apex 531a. In lower side wall portions 531c, 531c, reinforcing sheets 535 are disposed between the first and second liquid-permeable sheets 23a, 23b. In the projection 531, difference in stiffness is provided not only between the apex 531a and upper side wall portions 531b, 531b but also between the upper side wall portions 531b, 531b and the lower side wall portions 531c, 531c. Therefore, the opening angle θ between the upper side wall portions 531b, 531b can easily be set within the above range without providing the side elastic members.

Figure 12B:
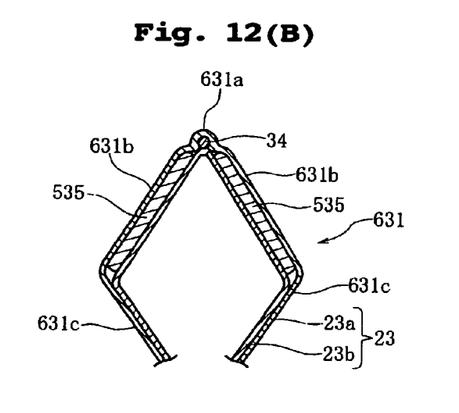

In the embodiment shown in FIG. 12(B), a projection 631 is formed of the topsheet 23 with the central elastic member 34 disposed between the first and second liquid-permeable sheets 23a, 23b to provide an apex 631a. Here, no side elastic members are provided. In upper side wall portions 631b, 631b, the reinforcing sheets 535 are disposed between the first and second liquid-permeable sheets 23a, 23b. As a result, difference in stiffness is provided between the upper side wall portions 631b, 631b and lower side wall portions 631c, 631c.

Here, it is possible not to provide the apex 631a with the central elastic member 34. If so, the topsheet 23 can be folded at the apex 631a more easily.

The reinforcing sheet 535 is preferably hydrophilic and, for example, may be an air-laid pulp nonwoven fabric in which pulp is fixed through a binder, an air-laid pulp nonwoven fabric in which rayon is mixed with the pulp, or another pulp sheet made by depositing and compressing pulp.

Figure 13A:
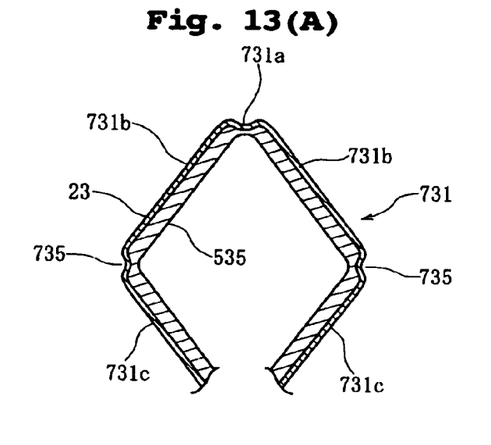
FIGS. 13(A) and 13(B) are partial sectional views showing other embodiments of a projection.

In the embodiment shown in FIG. 13(A), a projection 731 is not provided with the central and side elastic members. The projection 731 is formed of a laminate of the topsheet 23 and the hydrophilic reinforcing sheet 535 shown in FIG. 12. At an apex 731a, the topsheet 23 and the reinforcing sheet 535 are fusion-bonded under pressure to have a continuous groove along the longitudinal centerline Oy or recesses arranged intermittently along the longitudinal centerline Oy. The topsheet 23 and the reinforcing sheet 535 are likewise fusion-bonded under pressure at boundaries 735 between upper side wall portions 731b and lower side wall portions 731c.

As a result, difference in stiffness is provided between the apex 731a and the upper side wall portions 731b and between the boundaries 735 and the upper and lower side wall portions 731b, 731c. This facilitates folding of the laminate of the topsheet 23 and the reinforcing sheet 535.

Here, the topsheet 23 and the reinforcing sheet 535 may be just compressed along the apex 731a and the boundaries 735. Alternatively, such difference in stiffness may be provided by forming holes (or cuts) at longitudinally spaced intervals along the apex 731a and the boundaries 735, like perforation.

Figure 13B:
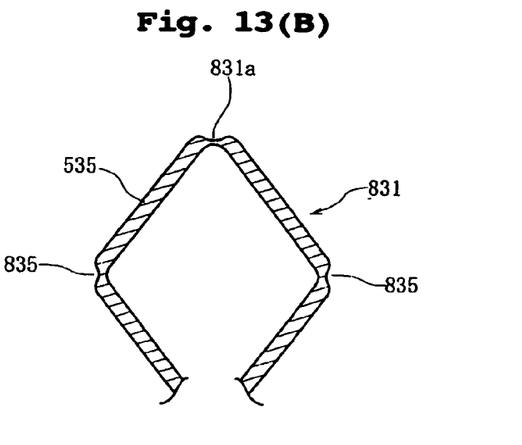

In the embodiment shown in FIG. 13(B), a projection 831 is formed of the reinforcing sheet 535 alone. The reinforcing sheet 535 is preferably an air-laid nonwoven fabric. Along an apex 831a and boundaries 835, the reinforcing sheet 535 is fusion-bonded, compressed, or cut to make a difference in stiffness.

Also in the embodiments shown in FIGS. 13(A) and 13(B), there may be provided the central elastic member and optionally the side elastic members.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but should be understood to include all possible embodiments which can be embodied within a scope encompassed and equivalent thereof with respect to the feature set out in the appended claims.

What is claimed is:

1. A sanitary napkin comprising:

a napkin body having a liquid-absorbent layer for absorbing and retaining liquid; and a projection projecting from a body surface of the napkin body, the projection having an apex and a pair of side wall portions formed of a liquid-permeable material, the apex being spaced apart from the body surface of the napkin body and extending along a longitudinal centerline of the napkin body, the side wall portions connecting at the apex and diverging toward the body surface of the napkin body, wherein the apex and the side wall portions are different in stiffness, and the side wall portions have a space therebetween and are permitted to deform and approach each other, wherein the side wall portions first diverge and subsequently converge from the apex toward the body surface of the napkin body, wherein the apex of the projection includes a longitudinally-extending central elastic member whose both ends are secured on the napkin body to exert a tension for causing deformation of the napkin body, wherein the projection further includes longitudinally-extending side elastic members on both sides of the central elastic member, wherein the central elastic member exerts a greater elastic tension than each side elastic members, and wherein the individual central and side elastic members have front and rear connection points between which the elastic member remains unsecured on the napkin body, the front connection point of each side elastic member is located behind the front connection point of the central elastic member, and the rear connection point of each side elastic member is located forward of the rear connection point of the central elastic member.

2. The sanitary napkin of claim 1, wherein the side wall portions are adapted to return to an opening angle of 20 degrees or more after removal of a compressive force of 2 kg per 10 cm × 10 cm, which is laterally applied to the projection for 30 seconds to bring the side wall portions into contact with each other.

3. The sanitary napkin of claim 1, wherein the projection is adapted to deform in accordance with deformation of the napkin body when front and rear ends of the napkin body approach each other to concavely curve the body surface of the napkin body.

4. The sanitary napkin of claim 3, wherein the central elastic member is spaced farther from the napkin body than the side elastic members, and the side wall portions extend between the central elastic member and the respective side elastic members.

5. The sanitary napkin of claim 1, wherein in a natural state where no external force is exerted on the napkin body, a height of the projection from the body surface of the napkin body is maximized at a location behind a vagina-facing part of the sanitary napkin.

6. The sanitary napkin of claim 1, wherein each side elastic member is positioned in one of the side wall portions between an edge of the side wall connecting at the apex and a boundary portion of the side wall which reaches the body side surface of the napkin body.

7. The sanitary napkin of claim 1, wherein a surface of the projection portion is formed with a sheet raised over a surface of the napkin body.

8. The sanitary napkin of claim 1, wherein the side elastic members are opposingly formed along the side wall portions at an outermost position of each side wall portion with respect to the longitudinal centerline of the napkin body.

* * * * *